(12) United States Patent  
Anwar et al.

(10) Patent No.: US 8,808,362 B2
(45) Date of Patent: *Aug. 19, 2014

(54) SYSTEM AND METHOD FOR PROVIDING A GRAFT IN A VASCULAR ENVIRONMENT

(75) Inventors: Azam Anwar, Dallas, TX (US); Georges A. Feghali, Ocean Springs, MS (US); Kenneth B. Johnson, Dallas, TX (US)

(73) Assignee: Graft Technologies, Inc., Dallas, TX (US)

( * ) Notice: Subject to any disclaimer, the term of this patent is extended or adjusted under 35 U.S.C. 154(b) by 5 days.

This patent is subject to a terminal disclaimer.

(21) Appl. No.: 12/756,361

(22) Filed: Apr. 8, 2010

(65) Prior Publication Data

US 2010/0191322 A1 Jul. 29, 2010

Related U.S. Application Data

(63) Continuation of application No. 11/483,121, filed on Jul. 7, 2006, now Pat. No. 7,722,665.

(51) Int. Cl.
*A61F 2/82* (2006.01)

(52) U.S. Cl.
USPC .......................................................... 623/1.36

(58) Field of Classification Search
USPC ................................................ 623/1.11–1.48
See application file for complete search history.

(56) References Cited

U.S. PATENT DOCUMENTS

| | | | |
|---|---|---|---|
| 4,794,928 A | 1/1989 | Kletschka | |
| 5,156,619 A * | 10/1992 | Ehrenfeld | 623/1.31 |
| 5,197,976 A | 3/1993 | Herweck et al. | |
| 5,443,497 A * | 8/1995 | Venbrux | 623/1.13 |
| 5,571,172 A | 11/1996 | Chin | |
| 5,591,226 A | 1/1997 | Trerotola et al. | |
| 5,647,857 A | 7/1997 | Anderson et al. | |
| 5,755,775 A | 5/1998 | Trerotola et al. | |
| 5,797,887 A | 8/1998 | Rosen et al. | |
| 5,800,522 A | 9/1998 | Campbell et al. | |

(Continued)

FOREIGN PATENT DOCUMENTS

| | | |
|---|---|---|
| EP | 0 246 341 | 5/1986 |
| EP | 0 334 567 | 3/1989 |

(Continued)

OTHER PUBLICATIONS

D. Kirsch, M.D., et al., "In Vitro Evaluation of Side-Branch Creation in Metal Stents by Balloon Dilation," *The Journal of Applied Research*, vol. 3, No. 4, Fall, 2003, pp. 380-387.

(Continued)

*Primary Examiner* — Suzette J Gherbi
(74) *Attorney, Agent, or Firm* — Patent Capital Group

(57) ABSTRACT

An apparatus is provided that includes a graft for coupling two vascular conduits within a patient. The graft includes: 1) an anchor system that forms an arc at one end of the conduits; and 2) a body element coupled to the anchor system. The anchor system comprises a biodegradable stent. In particular embodiments, portions of the graft are either self-expandable or balloon-expandable. In still other embodiments, anchor system includes NITINOL and the anchor system is substantially self-sealing at one end of the conduits. In one embodiment, the body element comprises polytetrafluoroethylene (PTFE) or expanded polytetrafluoroethylene (EPTFE). In yet other embodiments, the body element includes either a gelatinous or an elastomeric coating disposed on its surface.

21 Claims, 12 Drawing Sheets

(56) References Cited

U.S. PATENT DOCUMENTS

| | | | |
|---|---|---|---|
| 5,807,329 A | 9/1998 | Gelman | |
| 5,861,026 A | 1/1999 | Harris et al. | |
| 5,989,244 A | 11/1999 | Gregory et al. | |
| 5,989,276 A | 11/1999 | Houser et al. | |
| 5,990,379 A | 11/1999 | Gregory | |
| 6,001,117 A | 12/1999 | Huxel et al. | |
| 6,019,788 A | 2/2000 | Butters et al. | |
| 6,030,395 A * | 2/2000 | Nash et al. | 606/153 |
| 6,048,844 A | 4/2000 | Falk et al. | |
| 6,056,762 A | 5/2000 | Nash et al. | |
| 6,071,263 A | 6/2000 | Kirkman | |
| 6,110,188 A | 8/2000 | Narciso, Jr. | |
| 6,146,396 A | 11/2000 | Konya et al. | |
| 6,168,604 B1 | 1/2001 | Cano | |
| 6,187,038 B1 | 2/2001 | Sullivan et al. | |
| 6,221,101 B1 | 4/2001 | Harris et al. | |
| 6,248,117 B1 | 6/2001 | Blatter | |
| 6,261,316 B1 | 7/2001 | Shaolian et al. | |
| 6,372,228 B1 | 4/2002 | Gregory | |
| 6,379,380 B1 | 4/2002 | Satz | |
| 6,403,635 B1 | 6/2002 | Kinsella et al. | |
| 6,458,140 B2 | 10/2002 | Akin et al. | |
| 6,485,513 B1 | 11/2002 | Fan | |
| 6,497,729 B1 | 12/2002 | Moussy et al. | |
| 6,498,142 B1 | 12/2002 | Sampath et al. | |
| 6,589,278 B1 | 7/2003 | Harris et al. | |
| 6,605,053 B1 | 8/2003 | Kamm et al. | |
| 6,626,939 B1 | 9/2003 | Burnside et al. | |
| 6,663,667 B2 * | 12/2003 | Dehdashtian et al. | 623/1.51 |
| 6,726,923 B2 | 4/2004 | Iyer et al. | |
| 6,740,101 B2 | 5/2004 | Houser et al. | |
| 6,752,826 B2 | 6/2004 | Holloway et al. | |
| 6,800,089 B1 * | 10/2004 | Wang | 623/1.44 |
| 6,805,898 B1 | 10/2004 | Wu et al. | |
| 6,814,753 B2 | 11/2004 | Schmitt | |
| 6,852,122 B2 | 2/2005 | Rush | |
| 6,861,404 B1 | 3/2005 | Cohen et al. | |
| 6,913,762 B2 | 7/2005 | Caplice et al. | |
| 6,918,927 B2 | 7/2005 | Bates et al. | |
| 7,100,617 B1 | 9/2006 | Maginot | |
| 7,160,311 B2 | 1/2007 | Blatter et al. | |
| 7,232,459 B2 | 6/2007 | Greenberg et al. | |
| 7,351,247 B2 * | 4/2008 | Kupiecki et al. | 606/153 |
| 7,407,509 B2 * | 8/2008 | Greenberg et al. | 623/1.35 |
| 7,493,154 B2 | 2/2009 | Bonner et al. | |
| 7,722,665 B2 * | 5/2010 | Anwar et al. | 623/1.36 |
| 2001/0004697 A1 | 6/2001 | Blatter et al. | |
| 2001/0004698 A1 | 6/2001 | Blatter et al. | |
| 2001/0007931 A1 | 7/2001 | Blatter | |
| 2001/0027185 A1 | 10/2001 | Linden et al. | |
| 2001/0047197 A1 | 11/2001 | Foley | |
| 2002/0055539 A1 | 5/2002 | Bockow et al. | |
| 2002/0090388 A1 | 7/2002 | Humes et al. | |
| 2002/0090389 A1 | 7/2002 | Humes et al. | |
| 2003/0065345 A1 | 4/2003 | Weadock | |
| 2003/0065346 A1 | 4/2003 | Evens et al. | |
| 2003/0099682 A1 | 5/2003 | Moussy et al. | |
| 2003/0113359 A1 | 6/2003 | Iyer et al. | |
| 2003/0207907 A1 | 11/2003 | Iversen et al. | |
| 2004/0018228 A1 | 1/2004 | Fischell et al. | |
| 2004/0019315 A1 | 1/2004 | Blatter | |
| 2004/0138644 A1 | 7/2004 | DiCarlo et al. | |
| 2004/0161547 A1 | 8/2004 | Carlson et al. | |
| 2004/0163655 A1 | 8/2004 | Gelfand et al. | |
| 2004/0167572 A1 | 8/2004 | Roth et al. | |
| 2004/0167618 A1 | 8/2004 | Shaolian et al. | |
| 2004/0197409 A1 | 10/2004 | Iyer et al. | |
| 2004/0215125 A1 | 10/2004 | Brown | |
| 2004/0215220 A1 | 10/2004 | Dolan et al. | |
| 2004/0254419 A1 | 12/2004 | Wang et al. | |
| 2005/0002981 A1 | 1/2005 | Lahtinen et al. | |
| 2005/0004158 A1 | 1/2005 | Iyer et al. | |
| 2005/0033334 A1 | 2/2005 | Santra et al. | |
| 2005/0033417 A1 | 2/2005 | Borges et al. | |
| 2005/0059925 A1 | 3/2005 | Maginot et al. | |
| 2005/0084514 A1 | 4/2005 | Shebuski et al. | |
| 2005/0085557 A1 | 4/2005 | Wentworth et al. | |
| 2005/0131531 A1 | 6/2005 | Keenan | |
| 2005/0137677 A1 | 6/2005 | Rush | |
| 2005/0143304 A1 | 6/2005 | Cohen et al. | |
| 2005/0148512 A1 | 7/2005 | Hunter et al. | |
| 2005/0165475 A1 | 7/2005 | Noh | |
| 2005/0171598 A1 * | 8/2005 | Schaeffer | 623/1.35 |
| 2005/0178396 A1 | 8/2005 | Hunter et al. | |
| 2005/0181016 A1 | 8/2005 | Freyman et al. | |
| 2005/0181977 A1 | 8/2005 | Hunter et al. | |
| 2008/0009781 A1 | 1/2008 | Anwar et al. | |
| 2008/0132993 A1 * | 6/2008 | Rasmussen et al. | 623/1.13 |
| 2008/0208316 A1 | 8/2008 | Shalev et al. | |
| 2008/0241212 A1 * | 10/2008 | Moses et al. | 424/423 |
| 2009/0043377 A1 | 2/2009 | Greenberg et al. | |
| 2009/0076587 A1 | 3/2009 | Cully et al. | |
| 2009/0125095 A1 | 5/2009 | Bui et al. | |
| 2009/0131767 A1 | 5/2009 | Arne et al. | |
| 2009/0270978 A1 * | 10/2009 | Virkler et al. | 623/1.46 |
| 2010/0204776 A1 | 8/2010 | Anwar et al. | |
| 2010/0222870 A1 * | 9/2010 | Kaplan et al. | 623/1.35 |
| 2011/0313502 A1 * | 12/2011 | Granada et al. | 623/1.2 |

FOREIGN PATENT DOCUMENTS

| | | |
|---|---|---|
| EP | 1 364 627 | 2/1995 |
| EP | 1 258 229 | 5/2001 |
| WO | WO 01/80918 | 4/2000 |
| WO | WO 02/62335 | 1/2002 |

OTHER PUBLICATIONS

G. Kalmar, M.D., et al., "Radial Force and all Apposition of Balloon-expandable Vascular Stents in Eccentric Stenoses: An In Vitro Evaluation in a Curved Vessel Model," http://www.jvir.org/cgi/content/full/13/5/499, *Journal of Vascular and Interventional Radiology*, vol. 13, pp. 499-508, © 2000 *The Society of Cardiovascular & Interventional Radiology*; http://www.jvir.org/cgi/content/full/13-5-499; Printed Jun. 28, 2006.

W. Schmidt, et al., "Comparison of mechanical properties of peripheral self-expanding Nitinol and balloon-expandable stainless-steel stents," Electronic Poster, Annual Meeting and Postgraduate Course, Cardiovascular and Interventional Radiological Society of Europe (CIRSE), Barcelona, Spain, Sep. 29, 2004; 7 pages.

V. Hoang, "Stent Design and Engineer Coating Over Flow Removal Tool—Team #3 (Vimage)," Oct. 29, 2004, 9 pages.

Angiotech Pharmaceuticals, Inc., "Angiotech completes acquisition of Lifespan(R) vascular graft product line from Edwards Lifesciences," http://biz.yahoo.com/prnews/, Printed Dec. 1, 2005, 2 pages.

Ho-Wook Jun, et al., "Nitric Oxide-Producting Polyurethanes," © 2005 American Chemical Society, *Biomacromolecules*, vol. 6, No. 2, Published on Web Jan. 19, 2005, pp. 838-844.

Boston Scientific, "PTCA with Stent," http://www.bostonscientific.com, Printed Jun. 28, 2006, 9 pages.

J.I. Rotmans, et al., "Hemodialysis access graft failure: Time to revisit an unmet clinical need?" *Journal of Nephrology*, vol. 18, No. 1, http://www.sin-italy.org/jnonline/Vol18n1/9.html, Printed Aug. 4, 2006, 14 pages.

H. King, M.D., DSC, et al., "Global Burden of Diabetes, 1995-2025: Prevalence, numerical estimates, and projections," Diabetes Care, vol. 21, No. 9, Sep. 1998, pp. 1414-1431.

H.I. Feldman, et al., "Hemodialysis Vascular Access Mobility," Journal of the American Society of Nephrology, vol. 7, No. 4, 1996, pp. 523-535.

R.Y. Kanterman, M.D., et al., "Dialysis Access Grafts: Anatomic Location of Venous Stenosis and Results of Angioplasty," Interventional Radiology, vol. 195, No. 1, 1995, pp. 135-139.

M. Rekhter, et al., "Cell proliferation in human arteriovenous fistulas used in hemodialysis," Arteriosclerosis, Thrombosis, and Vascular Biology, vol. 13, No. 4, Jul. 11, 2006, cover page and pates 609-17.

P. Roy-Chaudhury, et al., "Venous neointimal hyperplasia in polytertrafluoroethylene dialysis grafts," , www.pubmed.gov (abstract only), Kidney Int., 59(6):2325-34, Printed Aug. 4, 2006.

(56) References Cited

OTHER PUBLICATIONS

S.H. Swedberg, et al., "Intimal fibromuscular hyperplasia at the venous anastomosis of PTFE grafts in hemodialysis patents, Clinical, immunocytochemical, light and electroni microscopic assessment," *Circulation*, vol. 80, No. 6, Jul. 11, 2006, cover page and pp. 1726-1736.

M.F. Weiss, et al., "Oxidative stress and increased expression of growth factors in lesions of failed hemodialysis access," www.pubmed.gov (abstract only), AmJ Kidney Dis., Jul. 25, 2006, 37(5):970-80.

A. Leuprecht, et al., "Numerical study of hemodynamics and wall mechanics in distal end-to-side anastomoses of bypass grafts," Journal of Biomechanics, vol. 35, pp. 225-236, © 2002.

W.M. Abbott, et al., "Effect of compliance mismatch on vascular graft patency," www.pubmed.gov (abstract only), J Vasc Surg., Jul. 25, 2006, 5(2):376-82.

W. Trubel, et al., "Compliance mismatch and formation of distal anastomotic intimal hyperplasia in externally stiffened and lumen-adapted venous grafts," www.pubmed.gov (abstract only), Eur. Vasc Endovasc Surg., Jul. 25, 2006, 10(4):415-23.

J.J. Castellot, Jr., et al., "Cultured Endothelial Cells Produce a Heparinlike Inhibitor of Smooth Muscle Cell Growth," Journal of Cell Biology, vol. 90, Aug. 1981, pp. 372-379.

P.L. McNeil, et al., "Growth Factors are Released by Mechanically Wounded Endothelial Cells," Journal of Cell Biology, vol. 109, Aug. 1989, pp. 811-822.

J.E. O'Brien, Jr., et al., "Early Injury to the Media after Saphenous Vein Grafting," The Annals of Thoracic Surgery, vol. 65, Issue 5, http://www.scincedirect.com (abstract only), © 1998, pp. 1273-1278.

G. Pertosa, et al., "Clinical relevance of cytokine production in hemodialysis," www.pubmed.gov (abstract only), Kidney Int Suppl., Jul. 25, 2006, 76: S104-11.

G.R. Grotendorst, et al., "Platelet-derived growth factor is a chemoattractant for vascular smooth muscle cells," www.pubmed.gov (abstract only), J Cell Physiol. Jul. 25, 2006, 113(2):261-6.

A.C. Newby, et al., "Molecular mechanisms in intimal hyperplasia," www.pubmed.gov (abstract only), J Pathol Jul. 25, 2006, 190(3):300-9.

V. Lindner, et al., "Role of basic fibroblast growth factor in vascular lesion formation," *Circ. Res.*, vol. 68, No. 1, Jul. 11, 2006, cover page and pates 106-13.

A. Jawien, et al., "Platelet-derived growth factor promotes smooth muscle migration and intimal thickening in a rat model of balloon angioplasty," www.pubmed.gov (abstract only), J Clin Invest., Jul. 25, 2006, 89(2):507-11.

M.J. Daemen, et al., "Angiotensin II induces smooth muscle cell proliferation in the normal and injured rat arterial wall," *Circ. Res.* vol. 68, No. 2, Jul. 11, 2006, cover page and pates 450-6.

H. Rakugi, et al., "Vascular injury induces angiotensinogen gene expression in the media and neointima," *Circulation*, vol. 87, No. 1, Jul. 11, 2006, cover page and pp. 283-290.

J.I. Rotmans, et al., "Rapid, arteriovenous graft failure due to intimal hyperplasia: a porcine bilateral, carotid arteriovenous graft model," www.pubmed.gov (abstract only), J Surg Res., Jul. 25, 2006, 113(1):161-71.

R. Dammers, et al., "Evaluation of 4-mm to 7-mm versus 6-mm prosthetic brachial-antecubital forearm loop access for hemodialysis: results of a randomized multicenter clinical trial," www.pubmed.gov (abstract only), J Vasc Surg. 37(1):143-8, Jan. 2003.

D. Mehta, et al., "External stenting reduces long-term medial and neointimal thickening and platelet derived growth factor expression in a pig model of arteriovenous bypass grafting," www.pubmed.gov (abstract only), Nat Med., 4(2):235-9, Feb. 1998.

P.J. Gagne, et al., "The effect of venous anastomosis Tyrell vein collar on the primary patency of arteriovenous grafts in patients undergoing hemodialysis," www.pubmed.gov (abstract only), J Vasc Surg. 32(6):1149-54, Dec. 2000.

J.E. Rosenman, et al., "Kinetics of endothelial seeding," www.pubmed.gov (abstract only), J Vasc Surg. 2(6):778-84, Nov. 1985.

M. Deutsch, et al., "Clinical autologous in vitro endothelialization of infrainguinal ePTFE grafts in 100 patients: a 9-year experience," www.pubmed.gov (abstract only), Surgery, 126(5):847-55, Nov. 1999.

R. Saran, et al., "Association between vascular access failure and the use of specific drugs: the Dialysis Outcomes and Practice Patterns Study (DOPPS)," www.pubmed.gov (abstract only), Am J Kidney Dis. 40(6):1255-63, Dec. 2002.

J.S. Kaufman, et al., "Randomized Controlled Trial of Clopidogrel plus Aspirin to Prevent Hemodialysis Access Graft Thrombosis," J Am Soc Nephrol. vol. 14, pp. 2313-2121, © 2003.

V.M. Rodriguez, M.D., et al., "Effects of Brachytherapy on Intimal Hyperplasia in Arteriovenous Fistulas in a Porcine Model," J Vasc Interv Radiol., vol. 13, No. 12, pp. 1239-1246, © 2002.

S. Sun, et al., "Inhibitory effect of brachytherapy on intimal hyperplasia in arteriovenous fistula," www.pubmed.gov (abstract only), J Surg Res. 115(2):200-8, Dec. 2003.

J. Barton, et al., "PhotoPoint photodynamic therapy inhibits intimal hyperplasia in arteriovenous access grafts," www.pubmed.gov (abstract only), Cardiovasc Radiat Med., 3(3-4): 147-51, Jul.-Dec. 2002.

J.I. Rotmans, M.D., et al., "Matrix metalloproteinase inhibition reduces intimal hyperplasia in a procine arteriovenous-graft model," http://www.sciencedirect.com (abstract only), J Vasc Surg., vol. 39, Issue 2, pp. 432-439, Feb. 2004.

M.P. Bendeck, et al., "Doxycycline Modulates Smooth Muscle Cell Growth, Migration, and Matrix Remodeling after Arterial Injury," *American Journal of Pathology*, vol. 160, No. 3, pp. 1089-1095, Nov. 14, 2001.

M.J. Englesbe, et al., "Concomitant blockade of paletelet-derived growth factor receptors alpha and beta induces intimal atrophy in baboon PTFE grafts," www.pubmed.gov (abstract only), J Vasc Surg. 39(2):440-6, Feb. 2004.

M.R. Kibbe, et al., "Adenovirus-mediated gene transfer of human inducible nitric oxide synthase in porcine vein grafts inhibits intimal hyperplasia," www.pubmed.gov (abstract only), J Vasc Surg., 34(1):156-65, Jul. 2001.

Hyun-Jai Cho, et al., "Mobilized Endothelial Progenitor Cells by Granulocyte-Macrophage Colony-Stimulating Factor Accelerate Reendothelialization and Reduce Vascular Inflammation After Intravascular Radiation," *Circulation*, 108:2918-25, Jul. 10, 2006.

J. Llevadot, et al., "HMG-CoA reductase inhibitor mobilizes bone marrow-derived endothelial progenitor cells," Journal of Clinical Investigation, vol. 108, No. 3, pp. 399-405, Aug. 2001.

D.H. Walter, et al., "Statin Therapy Accelerates Reendothelialization: A Novel Effect involving Mobilization and incorporation of Bone Marrow-Derived Endothelial Progenitor Cells," *Circulation*, vol. 105, cover page and pp. 3017-3024, Jul. 10, 2006.

V. Bhattacharya, et al., "Enhanced endothelialization and microvessel formation in polyester grafts seeded with CD34* bone marrow cells," Hemostasis, Thrombosis, and Vascular Biology, vol. 93, No. 2, pp. 581-585, Jan. 15, 2000.

G.A. Beathard, "Percutaneous transvenous angioplasty in the treatment of vascular access stenosis," www.pubmed.gov (abstract only), Kidney Int. 42(6):1390-7, Dec. 1992.

D. Vorwerk, M.D., et al., "Venous Stenosis and Occlusion in Hemodialysis Shunts: Follow-up Results of Stent Placement in 65 patients," *Radiology*, vol. 195, No. 1, pp. 140-146, 1995.

J.I. Rotmans, et al., "Sirolimus-Eluting Stents to Abolish Intimal Hyperplasia and Improve Flow in Porcine Arteriovenous Grafts: A 4-Week Follow-up Study," *Circulation*, vol. 111, cover page and pp. 1537-1542, Jul. 10, 2006.

M.C. Morice, et al., "A randomized comparison of a sirolimus-eluting stent with a standard stent for coronary revasculatization," www.pubmed.gov (abstract only), N Eng J Med., 346(23):1773-80, Jun. 2002.

A. Colombo, et al., "Randomized Study to Assess the Effectiveness of Slow- and Moderate-Release Polymer-Based Paclitaxel-Eluting Stents for Coronary Artery Lesions," *Circulation*, vol. 108, cover page and pp. 788-794, Jul. 10, 2006.

(56) References Cited

OTHER PUBLICATIONS

U.S. Appl. No. 12/756,395, filed Apr. 8, 2010, entitled "System and Method for Providing a Graft in a Vascular Environment", Inventor(s): Azam Anwar, et al.

Restriction Requirement in U.S. Appl. No. 11/483,121 mailed on Jun. 10, 2009.

Response to Restriction Requirement dated Jun. 10, 2009 in U.S. Appl. No. 11/483,121, filed Jun. 15, 2009.

Non-Final Office Action in U.S. Appl. No. 11/483,121 mailed on Jul. 29, 2009.

Response to Non-Final Office Action dated Jul. 29, 2009 in U.S. Appl. No. 11/483,121, filed Oct. 22, 2009.

Notice of Allowance in U.S. Appl. No. 11/483,121 mailed on Jan. 14, 2010.

Non-Final Office Action in U.S. Appl. No. 12/756,395 mailed on Aug. 23, 2011.

Response to Non-Final Office Action dated Aug. 23, 2011 in U.S. Appl. No. 12/756,395, filed Nov. 23, 2011.

Notice of Allowance in U.S. Appl. No. 12/756,395 mailed on Jan. 5, 2012.

\* cited by examiner

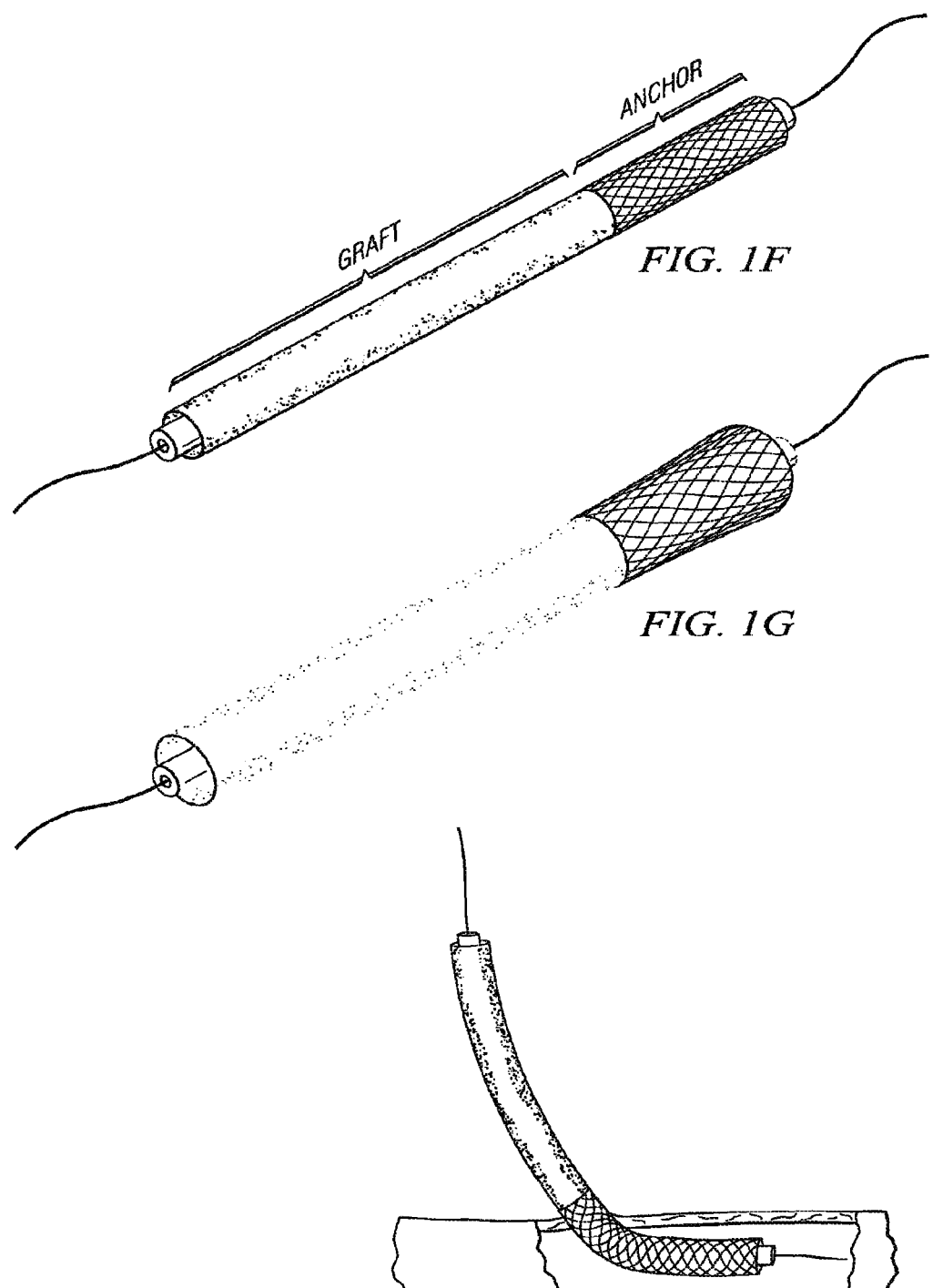

*FIG. 1I*
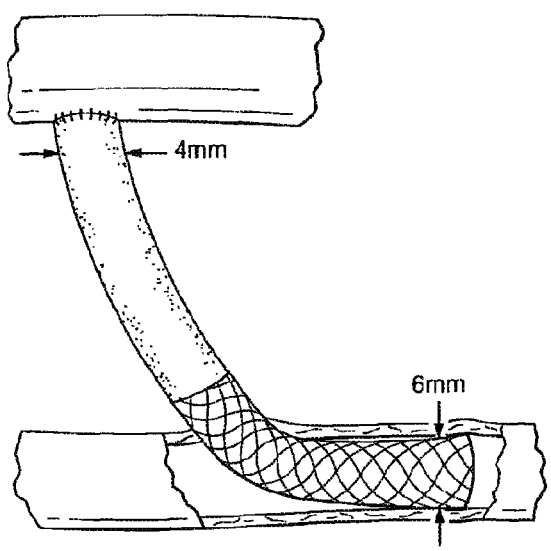
*FIG. 2A*
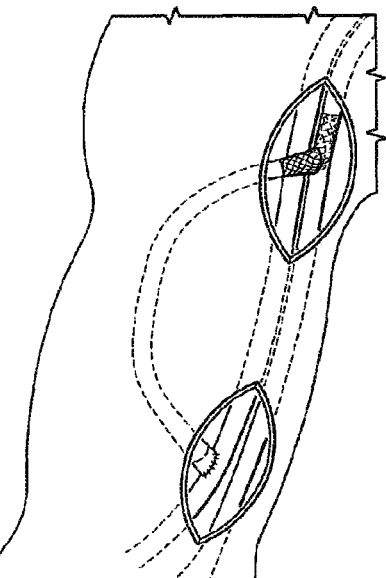
*FIG. 1J*   *FIG. 1K*
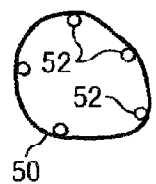 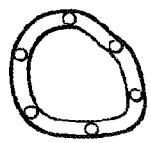
*FIG. 1L*
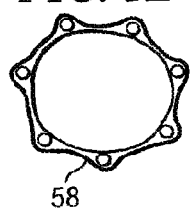

| POTENTIAL CONDUITS UTILIZED ARTERIOVENOUS ACCESS | | |
|---|---|---|
| CONDUITS | ADVANTAGES | DISADVANTAGES |
| POLYTETRAFLUOROETHYLENE (PTFE) | • NON-ANTIGENIC<br>• PATENCY EXCEEDED ONLY BY NATURAL FISTULAE<br>• GOOD HANDLING CHARACTERISTICS<br>• EASY TO THROMBECTOMIZE<br>• EASY TO CANNULATE | • RISK OF INFECTION HIGHER COMPARED WITH BIOLOGICAL GRAFTS |
| BOVINE CARTOID HETEROGRAFT | • PATENCY EQUIVALENT TO PTFE<br>• GOOD HANDLING CHARACTERISTICS | • INCREASED INCIDENCE OF ANEURYSM AND GRAFT DEGENERATION<br>• INCREASED COST<br>• INCREASED RISK OF INFECTION? |
| AUTOLOGOUS SAPHENOUS VEIN | • PATENCY EQUIVALENT TO PTFE<br>• RESISTANT TO INFECTION | • DIFFICULT TO CANNULATE<br>• VEIN HARVEST INCREASES OPERATIVE COMPLEXITY AND HOSPITALIZATION<br>• SACRIFICES POTENTIAL CONDUIT FOR CORONARY OR LIMB BYPASS |
| HOMOLOGOUS SAPHENOUS/ SUPERFICIAL FEMORAL VEIN | • PATENCY EQUIVALENT TO PTFE<br>• RESISTANT TO INFECTION? | • INCREASED COST<br>• INCREASED INCIDENCE OF ANEURYSM AND GRAFT DEGENERATION<br>• IMMUNOGENICITY MAY PRECLUDE TRANSPLANTATION |
| HUMAN UMBILICAL VEIN | • NONE | • INCREASED COST<br>• INCREASED INCIDENCE OF ANEURYSM AND GRAFT DEGENERATION?<br>• EXPERIENCE WITH GRAFT FOR AV ACCESS LIMITED |
| DACRON | • EXCELLENT TISSUE INGROWTH<br>• PATENCY EQUIVALENT TO PTFE? | • MORE DIFFICULT TO CANNULATE<br>• EXPERIENCE WITH GRAFT FOR AV ACCESS LIMITED<br>• THROMBECTOMY DIFFICULT |

*FIG. 2B*

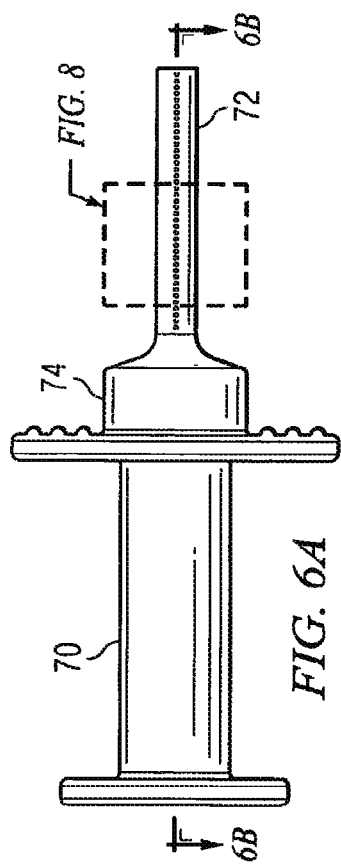
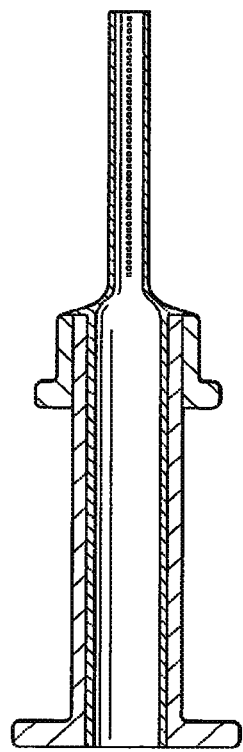
FIG. 5
FIG. 6A
FIG. 6B

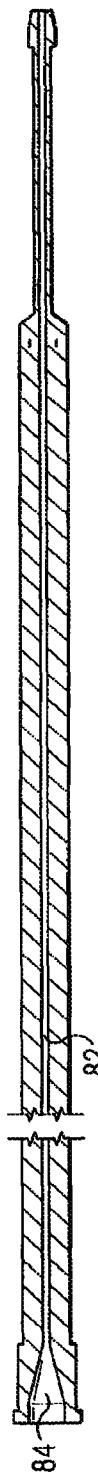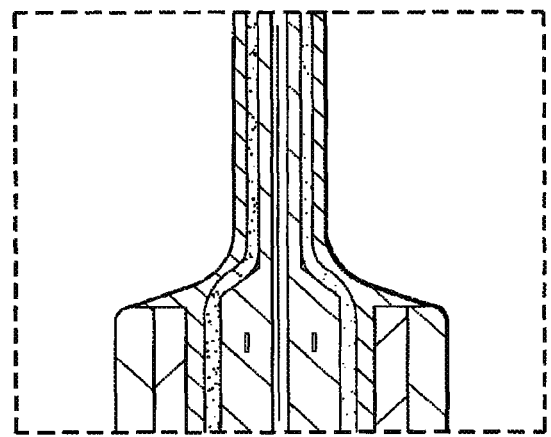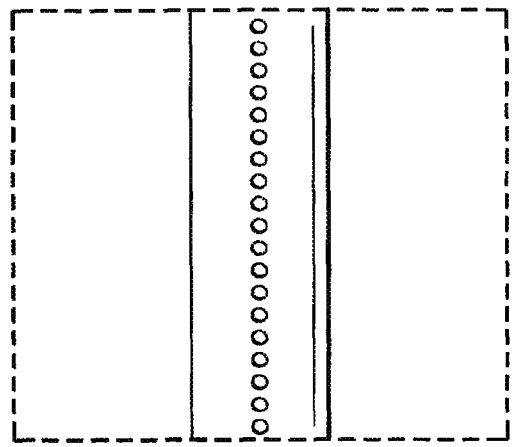
FIG. 7A
FIG. 7B
FIG. 9
FIG. 8

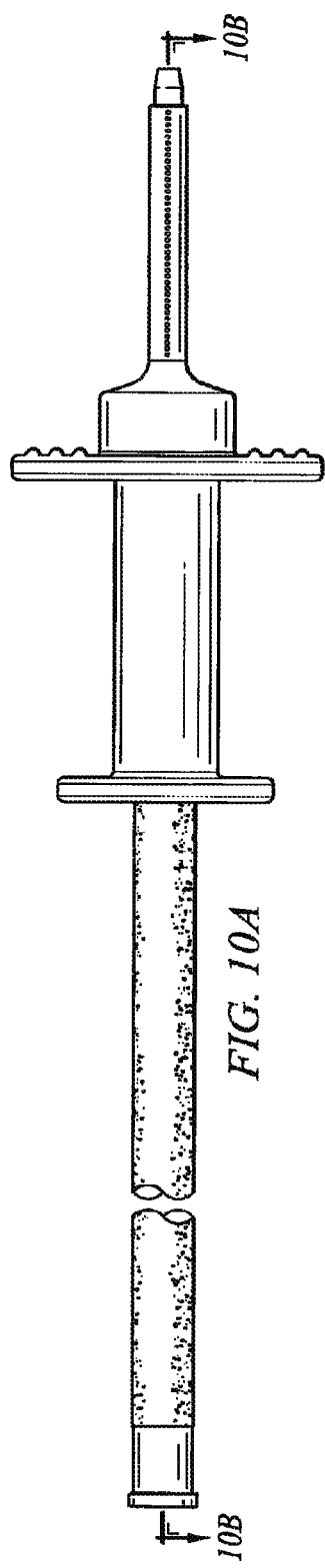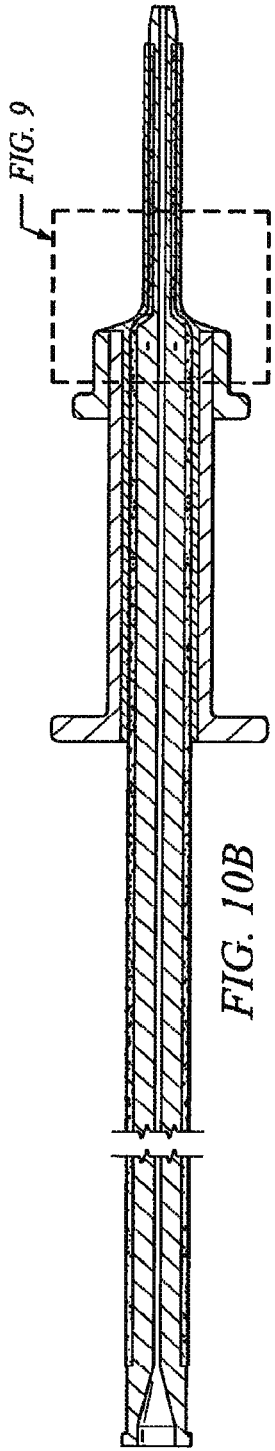

', '# SYSTEM AND METHOD FOR PROVIDING A GRAFT IN A VASCULAR ENVIRONMENT

RELATED APPLICATIONS

This Application is a continuation (and claims the benefit of priority under 35 U.S.C. §120) of U.S. application Ser. No. 11/483,121, filed Jul. 7, 2006, now U.S. Pat. No. 7,722,665 entitled "SYSTEM AND METHOD FOR PROVIDING A GRAFT IN A VASCULAR ENVIRONMENT," Inventor(s) Azam Anwar, et al. The disclosure of the prior application is considered part of (and is incorporated by reference in) the disclosure of this application.

TECHNICAL FIELD OF THE INVENTION

This invention relates in general to vascular procedures and, more particularly, to a process, a system, and a method for providing a graft in a vascular environment.

BACKGROUND OF THE INVENTION

The treatment of vascular diseases has grown exponentially in terms of sophistication and diversity. Procedures involving items such as stents or balloons are virtually routine in many health-care practices. However, despite vast advancements in many vascular procedures and medical devices, one particularly troublesome issue has remained in the field of kidney dialysis.

The number of patients requiring hemodialysis treatment grows at an alarming rate. Because patients generally require treatment until death or until kidney transplantation, the projection for the number of future hemodialysis procedures increases with each new group of patients.

Augmenting this problem is the prevalence of diabetes, which contributes directly to the number of patients requiring some form of kidney dialysis treatment. Currently, statistical data indicates that approximately twenty (20) million Americans have chronic kidney disease (CKD), while another twenty (20) million are at risk. Projections for the current population of patients with end-stage renal disease (ESRD) (which represents CKD patients requiring dialysis) are disturbing: reaching nearly 325,000 in 2002 with more than 100,000 patients beginning dialysis in 2003. Conservative estimates indicate that the prevalent rate of patients with ESRD is growing at approximately 3% per year and this rate is significantly higher in older populations (e.g. the 45-64 year range).

Concisely stated, current dialysis grafts are simply not ideal for a multitude of reasons. Many of the current shortcomings are described below in greater detail. These grafts can cause setbacks to the patient due to poor instrument design, adverse reactions from the patient's body, and higher costs for all individuals involved.

Accordingly, the ability to properly address vascular issues involving conduits within a suffering patient presents a significant challenge for device manufacturers, physicians, and surgeons alike.

SUMMARY OF THE INVENTION

From the foregoing, it may be appreciated by those skilled in the art that a need has arisen for an improved process for achieving superior flow, minimal stenosis, and optimal patency in a given vascular environment. In accordance with an embodiment of the present invention, a device, a system, and a method for facilitating optimal connections are provided that substantially eliminate or greatly reduce disadvantages and problems associated with conventional vascular devices, approaches, and strategies.

According to an embodiment of the present invention, an apparatus is provided that includes a graft for coupling two vascular conduits within a patient. The graft includes: 1) an anchor system that forms an arc at one end of the conduits; and 2) a body element coupled to the anchor system. The anchor system comprises a stent, which may be biodegradable, bioabsorbable, or biostable. In particular embodiments, portions of the graft are either self-expandable or balloon-expandable. In still other embodiments, the anchor system includes NITINOL and the anchor system is substantially self-sealing at one end of the conduits. The body element comprises polytetrafluoroethylene (PTFE), expanded polytetrafluoroethylene (EPTFE), polyurethane derivatives, or any other suitable materials. In yet other embodiments, the body element includes either a gelatinous or an elastomeric coating disposed on its surface.

In still yet other embodiments, the body element includes two materials, whereby one of the materials biodegrades at a rate that is different from the other material. Additionally, both the body and the anchor may include a coating or a wrap to be used for drug loading and drug alluding.

In more specific embodiments, the graft may be accompanied by a delivery system that is used to direct the graft to a target location, the delivery system including a perforated sheath, a plunger, and a base that is coupled to the plunger, whereby actuation of the plunger can direct the graft to its target location. There are a myriad of possible design choices for the present invention, many of which are detailed below. The audience should be aware that the present invention is replete with potential design elections/alternatives or deviations from the specifications or examples provided herein in this document. Accordingly, the present invention and its appended claims should be construed to encompass all such modifications.

Certain embodiments of the present invention may provide a number of technical advantages. For example, according to one embodiment of the present invention, an architecture and a process are provided that offer a flexible AV graft system for a surgeon to utilize. The graft includes a hemodynamic profile, which reduces scarring or occlusion-type complications that would otherwise arise. In addition, the graft of the present invention offers a unique anchoring system that is stable and that is not prone to subsequent intimal hyperplasia. Many existing graft systems produce unwelcome radial forces, which present a significant danger to the patient. The present invention overcomes these deficiencies (as well as others) because the anchor of the graft can be secured within the vessel (vein or artery): yielding minimal radial forces. Radial forces must be accounted for because they can serve to injure vessels. In an ideal scenario, the graft is self-sealing; although various types of sutures can be used if this is not the case. In one example embodiment, an abrasive material can be used to create enough frictional force that the anchor is stabilized.

Moreover, the graft structure of the present invention is advantageous because it can be leveraged to deliver drugs locally: either through a stent, an anchoring system, the body of the graft, a coating, a wrap, or any other suitable element. Due to many of the aforementioned beneficial characteristics, the architecture of the present invention can provide a new graft solution with significantly higher long-term patency rates.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIGS. 1D-1G are simplified schematic diagrams illustrating an example deployment of the graft;

FIGS. 1H-1I are simplified schematic diagrams of the graft being implemented in one example scenario;

FIGS. 1J-1L are simplified schematic diagrams illustrating several example implementations of an anchor of the present invention;

FIG. 2A is a simplified schematic diagram of a patient's arm after the connections have been formed;

FIG. 2B is a chart that depicts disadvantages and advantages of potential conduits utilized in arteriovenous access situations;

FIGS. 5-12D are simplified schematic diagrams illustrating one set of dimensions and/or design possibilities for the graft and delivery system of the present invention.

DETAILED DESCRIPTION OF THE INVENTION

Figure 1A:
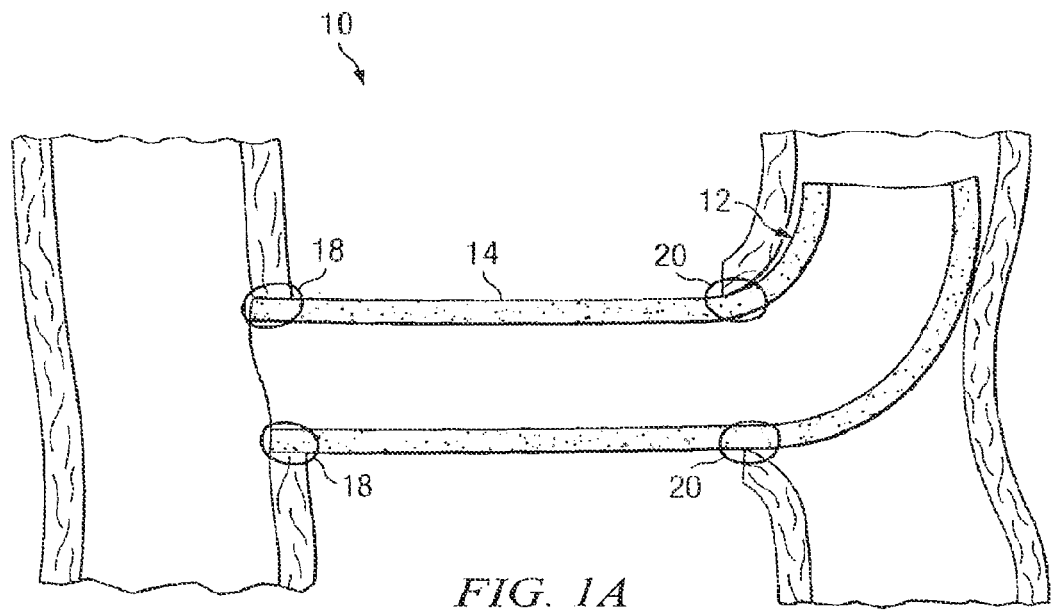
FIG. 1A is a simplified schematic diagram illustrating a vein and an artery, which may subjected to an example vascular procedure using a graft in accordance with one embodiment of the present invention.

For purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention, its potential applications, and the appended claims.

For patients with end stage renal disease (ESRD), dialysis helps to remove waste, to balance certain chemicals in the blood, to remove excess fluid, and to control blood pressure. The survival of patients with ESRD is dependent on dialysis. There are two modalities of dialysis: hemodialysis and peritoneal dialysis, the former being the most common modality. In order to perform a hemodialysis procedure, a large vascular access is required. There are several methods of access available, several of which are outlined below.

Hemodialysis catheters are used in virtually all new patients, while they await the maturation of their permanent treatment method using an arteriovenous (AV) fistula or AV graft. A fistula is a tube-like passage that extends from a normal cavity or tube to a free surface or to another cavity. Fistulas are generally desirable as a long-term treatment method. However, there are drawbacks with fistulas because: 1) there is a limited number of vessels in many patients; 2) there is a high likelihood of failure in diabetics; 3) there are few favorable veins in diabetics (i.e. veins having sufficient width and elasticity); and 4) the problem of intimal hyperplasia at the venous anastomosis is still present.

Current AV grafts are used primarily when AV fistulas are not recommended due to age considerations or diabetic conditions. However, the development of a new type of AV graft with higher patency rates could make grafts the preferred method of access for hemodialysis. Another advantage of grafts is that grafts can be used almost immediately (such that puncturing of the graft is readily permitted), whereas fistulas need considerably more time.

Because most of the growth in hemodialysis patients is due to diabetes or due to patient age (ranging from 45 to 64 years old), the current AV fistula method is often not a viable option. Therefore, a growing number of patients require AV grafts. However, current graft solutions are problematic, as they have unacceptably low long-term patency rates.

The present invention overcomes these problems (and others) in providing an ideal graft that addresses the issues presented above. The proposed solution of the present invention introduces a new type of AV graft. The main benefits of the new graft are a hemodynamic profile, a unique anchoring system, an ability to deliver drugs, and an improved construction, which can accommodate the use of a biodegradable material. The architecture of the present invention also offers a new AV graft solution with significantly higher long-term patency rates and which is much safer for the patient.

Note that the most common cause of graft failure is stenosis of the outflow vein, resulting in graft thrombosis. Modalities to treat failed grafts include: 1) surgery; 2) angioplasty with balloons and/or stents; and 3) declotting using devices or drugs. The surgical revision using a jump graft may extend the access further up the arm to a more central location. However, after angioplasty, the access is immediately available for use and the available veins are saved for future use. Also, angioplasty is an easy and safe procedure, representing a superior solution, which is in contrast to repeated surgical revisions. A recent study has shown a 77% reduction in the intimal hyperplasia at the venous anastomosis using sirolimus-eluting stents, as compared to bare metal stents. The graft patency after an initial intervention is approximately 40%. As expected, longer stenoses and those lesions that have been dilated several times have less favorable patency rates.

In regards to the treatment of a clotted graft, the pulse-spray pharmacomechanical thrombolysis (PSPMT) helps to salvage around 75-94% of grafts. Statistical evidence suggests that the primary patencies range from 24% to 34% at 6-months and the secondary patencies may reach 80%. Thrombectomy devices have increased the efficiency and speed of thrombus removal and, in certain cases, obviate the use of thrombolytics. After a thrombectomy, the venous outflow stenosis should be treated. Thrombectomy of an infected graft is an absolute contra-indication since revascularization may lead to fatal sepsis. However, signs of infections can be very subtle and an infection can be missed. Other complications of thrombectomy include: anemia, bleeding, acute cardiac events, and venous and arterial embolism.

The proposed "Ideal Graft" of the present invention is a device that offers an optimal flow profile (producing minimal turbulence), that acts as a backbone for endothelial progenitor cells seeding (EPCs seeding), and that anchors to the vein through a system that can deliver anti-proliferate, anti-thrombotic, anti-platelet, and anti-inflammatory agents to the surrounding tissues. The graft's body and/or anchor can be biodegradable and the system, in certain embodiments, is sutureless, as outlined in greater detail below. The inside of the graft's body and/or anchor can be coated with anti-coagulants, anti-platelets, or thrombolytics. The present invention has advantages over existing systems because of its placement into a vessel, the two-component system (anchor and body), and all the potential design configurations that could be accommodated by such a device. In addition, the present invention can readily be used in artery-vein connections, vein-vein connections, and artery-artery connections (e.g. potentially involving the lower extremities). Many of the potential design choices are further detailed below with reference to the FIGURES.

Turning back to FIG. 1A, in one embodiment, device 10 is a graft that includes two parts: anchor 12 and body 14. These pieces are integral or, in other embodiments, can be separated or connected in any other suitable manner. The graft can be made of expanded polytetrafluoroethylene (ePTFE) or PTFE: both of which represent a bio-stable substance that can be optimal in many vascular applications. More specifically, ePTFE is a hydrophobic material that offers superior waterproof performance.

Because repeat puncturing presents a significant bleeding issue for the patient [i.e. there is a sealing problem], the ePTFE can be coated with an elastomeric, gelatinous, or membrane that better accommodates improved sealing and a subsequent repuncture. ePTFE could be punctured immediately after being placed. In addition, ePTFE is beneficial because it is porous (which further allows tissue to grow directly on the device) and because it can be sewn into the vein. Tissue growth would essentially close the pores of the ePTFE.

Note that two preeminent considerations in constructing the graft are flow dynamics and the optimal delivery of drugs. For the patient, scarring would commence immediately after the procedure was performed and, hence, the drug aspect of the device is crucial. Venous stenosis will present a significant issue for both the patient and the physician; however the acuteness of this issue will be lessened considerably by optimal drug applications. The graft itself will stabilize with in-growth, shortly after placement.

The use of sutures will assist in this stabilization. Such sutures may be of a conventional type, purse string, interrupted sutures, or they may use a screw-type configuration in which pressure applied to the head of the suture translates into a rotational force that secures/tightens an intermediate object in place. In an ideal scenario, the graft secures itself (i.e. self-sealing) after the dilator and the splittable sheath are removed from the target site, whereby little of the graft anchor (e.g. NITINOL or any other suitable composite) is left exposed. However, in cases where stabilization is tenuous, then suturing (either at points 18, or 20 on the venous side where the anchor system is present) would be performed.

Figure 1B:
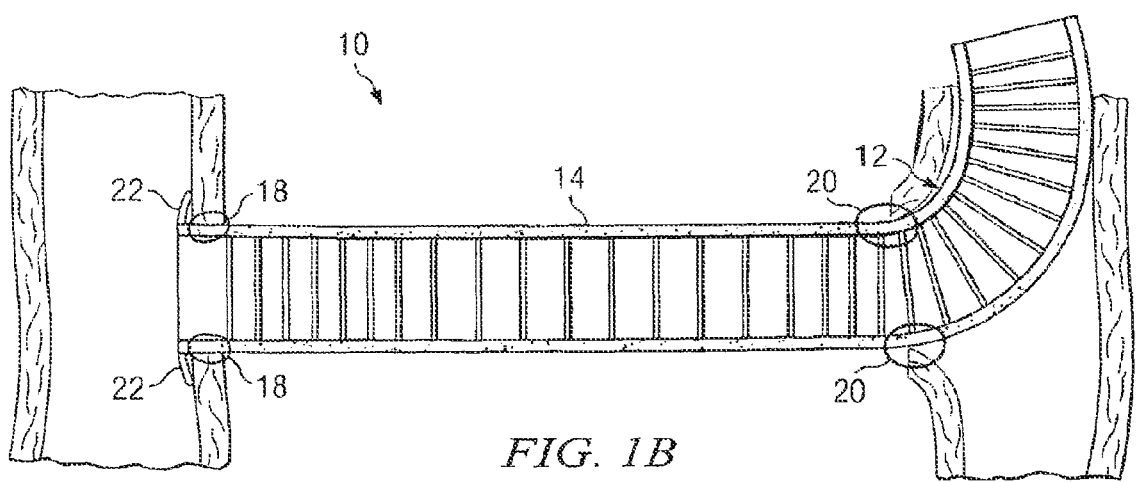
FIG. 1B is a simplified schematic diagram of the graft in which the body of the device is reinforced.
Figure 1C:
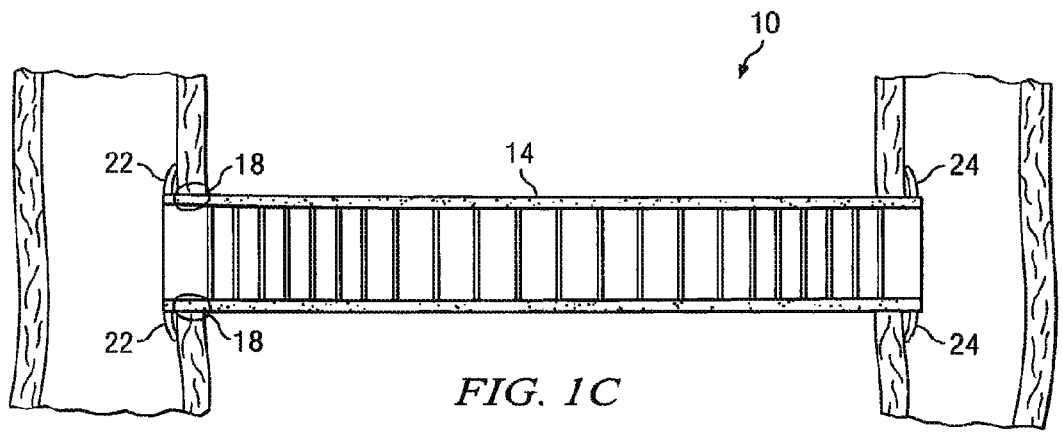
FIG. 1C is a simplified schematic diagram of an alternative embodiment of the graft in which each side of the device is suitably secured to the vein and the artery.
Figure 1D:
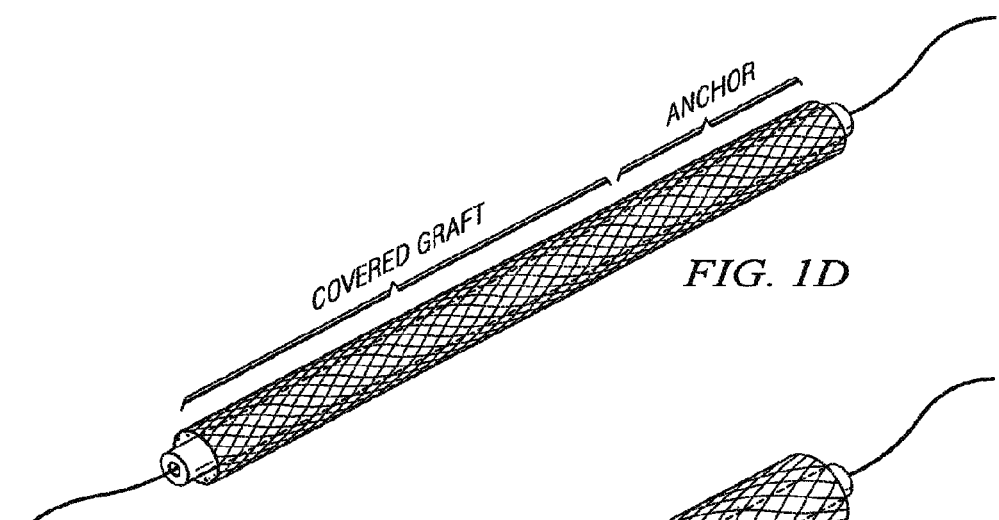
Figure 1E:
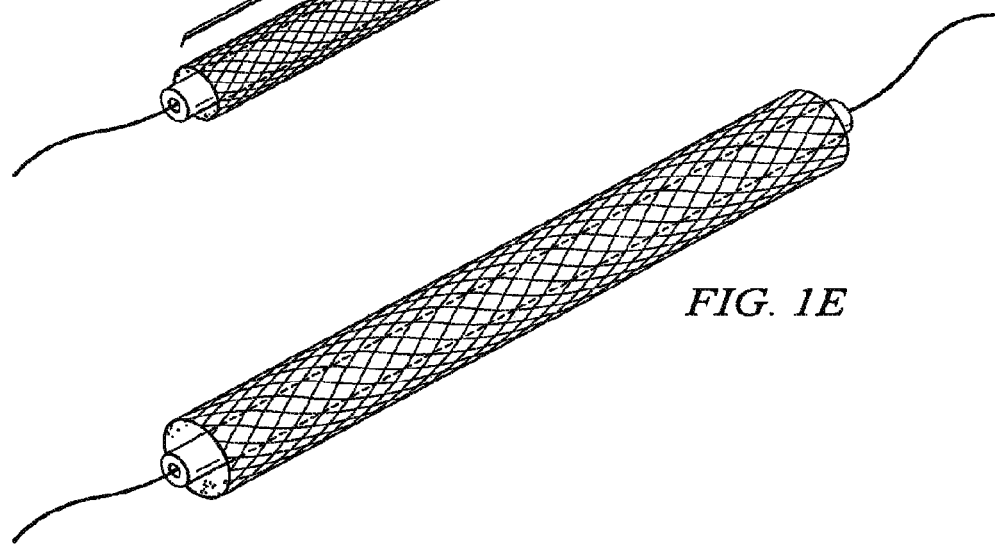

FIG. 1B is a simplified schematic diagram of the graft in which body 14 of device 10 is reinforced with internal scaffolding. FIG. 1B also illustrates the use of footers 22, which can assist in securing the graft in place. FIG. 1C is a simplified schematic diagram of an alternative embodiment of the graft in which each side of device 10 is suitably secured to the venous and arterial sides of the connection using footers 22 and 24. In still other scenarios, circumferential hooks, legs, or tines can be used to better fixate the device.

In order to avoid kinking, spatulation techniques may be employed. In addition, an abrasive material (either a coating or the underlying structure itself) may be used to seat the device. This material could provide a frictional resistive force that would inhibit movement on the anchor side where stabilization is more tenuous.

FIGS. 1D-1G are simplified schematic diagrams illustrating an example deployment of the graft. FIGS. 1H-1I are simplified schematic diagrams of the graft being implemented in one example scenario. Essentially, the device can be composed of two components: 1) the body of the graft (where the dialysis machine will be hooked and where dialysis takes place); and 2) the anchor, which will anchor the graft inside the vein. The body of the graft can include a stent graft, whereby the cells are large enough to enable the dialysis staff member to puncture the graft with a needle. Alternatively, the graft can be made of a regular graft (without a stent), which is attached to the anchor.

As evidenced by FIGS. 1H-1I, the graft can be anchored within the vein and not necessarily to the vein. This is important for reducing a number of potential patient complications. The opening where the graft would enter the vein is approximately 3 millimeters, but this parameter could change considerably due to specific patient/vein characteristics. Additional details relating to other example procedures and configurations are provided below.

In one embodiment, the graft is constructed of a self-expandable NITINOL anchor, which can readily be compressed before the device is placed. In other embodiments, the NITINOL could be replaced by any other suitably metal or alloy. In certain instances, NITINOL may be prone to fracturing and thus, other metals may be used without departing from the spirit and scope of the present invention. Virtually any material that gives structural integrity to the graft can be used. The expansion property of the anchor would allow the venous side to expand over time. The radial strength can be selected based on matching potential compliance with the vein or specific vein characterizes. For placement of the graft, the NITINOL anchor portion would be suitably compressed and then insertion of the device would occur on the venous side.

In particular embodiments, the proposed graft anchor is constructed of a biodegradable material that can dissolve (to varying degrees) in the body of the patient. Note that the cover or shell of the graft could be biodegradable, whereby an underlying latticework structure is used that is not biodegradable. This represents the use of at least two materials. In such a case, the underlying structure could be spiral or cylindrical, such as that depicted by FIGS. 1B-1C, or the underlying structure may be of any other requisite shape. One configuration could be underlying structure, drug, dissolvable barrier, or any other suitable combination thereof. The outer layer could be any suitable material such as those materials disclosed in U.S. Pat. No. 7,033,603, entitled: Drug Releasing Biodegradable Fiber for Delivery of Therapeutics; U.S. Pat. No. 6,858,222, entitled: Fabrication of Drug Loaded Biodegradable Polymer Fibers; and U.S. Pat. No. 6,596,296, entitled: Drug Releasing Biodegradable Fiber Implant. Some other possible configurations are further explained below.

In certain instances, the entire graft could be biodegradable. Hence, the graft could be partially biodegradable or fully biodegradable. It should also be recognized that two different biodegradable materials could be used in combination such that one material could dissolve more slowly than the other material. The slower dissolving material could function as a backbone or a skeleton for the graft: providing support for the device as it acclimates to its new environment. Any such permutations are clearly with the broad scope of the present invention.

In one embodiment, anchor 12 comprises a biodegradable material such that, over time, anchor 12 would dissolve at a selected pace. Any drug agent could be used to facilitate a dissolution objective of anchor 12. A coating or a wrap (e.g. a polymer, a fibrous material, etc.) could be used to assist in the drug deliver and/or assist in connecting or supporting anchor 12. Thus, in one example scenario, a simple polymer could be used on the surface of anchor 12 to inhibit fibrointimal hyperplasia (i.e. excessive growth of tissue).

Body 14 could comprise ePTFE, a polyurethane derivative, an elastomeric composite, or a gelatinous material. In one example, body 14 is not necessarily biodegradable such that it maintains its structural integrity. Other embodiments however allow body 14 to biodegrade (to varying degrees).

In terms of placement of the graft and its potential design [in the artery and vein combination embodiment], body 14 could be in the range of 3-9 millimeters in one example. Anchor 12 could extend 1-60 centimeters into a vessel (artery or vein) once it has been positioned. In general, there is little downside risk to having the anchor extend further into the vessel, as opposed to less. The longer the anchor, the more stable the device. Some obvious drug applications for the anchor would include heparin or any other suitable anticoagulant or anti-platelet.

The arc created by anchor 12 could be of any suitable degree measurement (e.g. 45 degrees), but in any event, should universally be gradual or smooth. The smoothness of the arc will facilitate a preferred hemodynamic profile. If the angle is too acute, the system will clot off, which is undesirable. A 90-degree angle, for example, would not be ideal and may cause the graft to kink or cause blood turbulence. The actual thickness or diameter of anchor 12 and/or body 14 could be in the range of 3-6 millimeters, while the small lip formed by the vein on one end of body 14 could be approximately 1.5 millimeters. Note that all of these specifications are only being provided by way of example. These measurements may be departed from considerably while still achieving the teachings of the present invention.

One important issue in procedures involving the graft of the present invention involves exposing the vein to various drugs, which can assist in the healing process and/or inhibit complications that normally occur in dialysis scenarios. In general, the venous side is more problematic and, hence, higher dosages of drugs should be delivered there. Such drug applications could have dosages that release over long periods of time; ideally, the longer the drug delivery, the better. It should also be noted that the selection of veins is critical. Veins less than 2 millimeters would probably not be feasible for such a graft procedure. Vein selection could be aided by sonography or other adequate technologies. It should also be noted that a Seldinger approach may be preferred to a simple veinotomy.

FIGS. 1J-1L are simplified schematic diagrams illustrating example implementations of anchor 12. In FIG. 1J, there are a number of struts 52 of an associated stent. An exterior cover 50 is biodegradable, bioabsorbable, or biostable. Note that any of the materials in these components could include drugs disposed directly thereon, or inherent within, such that the drug releases over time. This exterior material could include materials such as polyurethane, ePTFE, or a simple plastic/rubber derivative.

FIG. 1K illustrates the scenario in which two materials envelop the stent in a sandwich configuration. FIG. 1L illustrates an example in which a polymer 58 surrounds a stent (or any other suitable structure). The polymer can carry the drug and/or dissolve over a certain time period. It should be evident to the audience at this juncture in the Specification that the present invention is replete with potential design choices. The use of polymers, drugs, coatings, wraps, polyurethane derivatives, gelatinous, and elastomeric materials, stents, tubes, ePTFE, PTFE, and Dacron, etc. each represent a design choice that may be applicable for a given environment or scenario. The present invention encompasses any and all combinations of these elements. For purposes of brevity, the inventors have only provided an example set of devices for purposes of teaching and discussion.

FIG. 2A is a simplified schematic diagram of a patient's arm after the connections have been formed by the attending surgeon. Note that the dissolution of the graft will cause new endothelial cells to replace the structure of the graft. The endothelium is the layer of thin flat cells that lines the interior surface of blood vessels, forming an interface between circulating blood in the lumen and the rest of the vessel wall. Endothelial cells line the entire circulatory system, from the heart to the smallest capillary. In small blood vessels and capillaries, endothelial cells are often the only cell-type present. Hence, endothelial cells can help to form a new latticework for facilitating the blood flow in this area of a patient. Fibrous tissue is the other component in such a paradigm: together the fibrous tissue and the endothelial, cells function to enhance necessary conduit at this site.

FIG. 2B is a chart that depicts disadvantages and advantages of potential conduits utilized in arteriovenous access situations. Additionally, there could be any number of combinations of these conduit materials, which can be employed by the present invention. For example, the graft can be both constructed of Dacron and ePTFE in an alternative embodiment. In essence, any number of possible permutations and/or additional materials could be used for the graft.

Figure 3A:
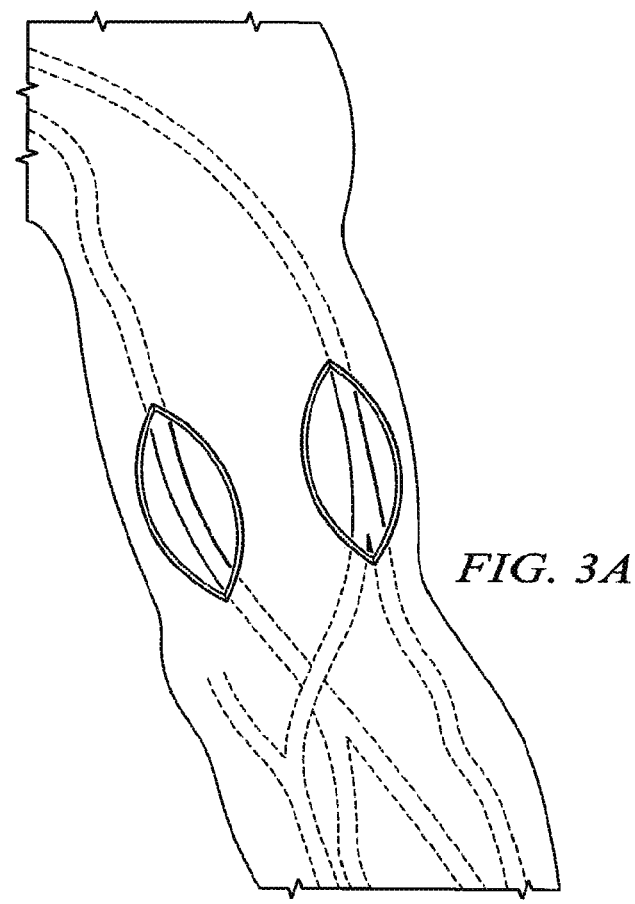
FIGS. 3A-3B are simplified schematic diagrams that illustrate an example of a patient's arm before and after a procedure involving the present invention has been performed.
Figure 3B:
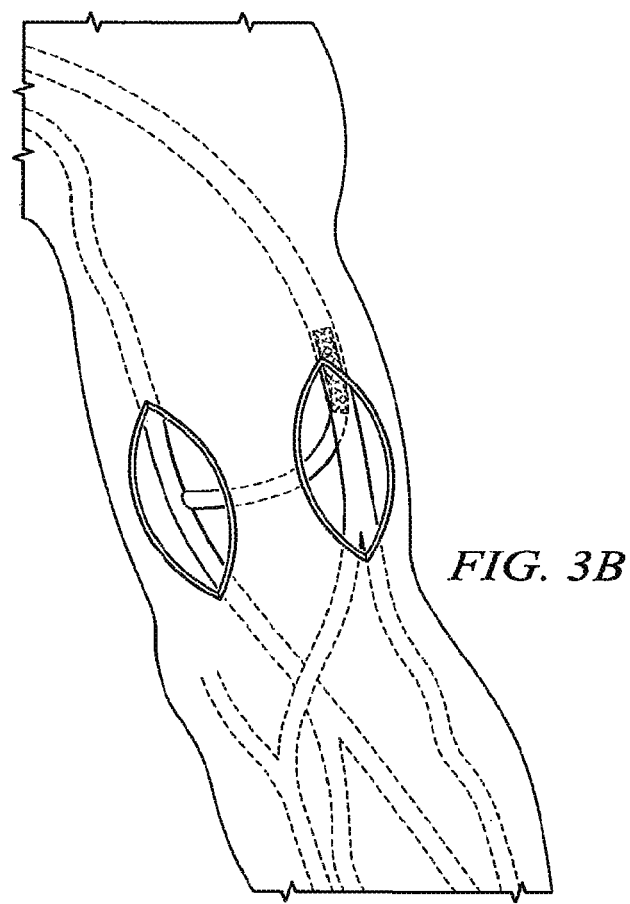

FIGS. 3A-3B are simplified schematic diagrams that illustrate an example of a patient's arm before and after a procedure involving the present invention has been performed. In operation, anchor 12 can be inserted into a vein and secured within the vein. The anchor system is a self-expandable or balloon-expandable biodegradable drug-eluting stent. The polymer with the active drug can cover the external surface of the stent. In certain embodiments, the anchor system can be used to anchor a vein to an artery or, alternatively, to another vein.

One function of anchor 12 is to ensure that the graft is attached to the vein. In still another example deployment, anchor 12 is positioned about 2-3 centimeters into the vein. Anchor 12 is designed such that, in its compressed or delivered state, it is relatively small in comparison to the point of entry. The material of anchor 12 has a memory such that when a surgeon releases it at the appropriate location, it will occupy a much larger area. Hence, once anchor 12 has been inserted into the vein, it can be deployed or expanded such that is provides an appropriate resistive force, pressure, or friction, which enables anchor 12 to be somewhat resistant to movement. This feature of anchor 12 minimizes radial forces and hyperplasia issues at this site.

Note that the vein in this example does not have to be necessarily ligated. The positioning of the graft obviates the need to perform additional ligating procedures that address small branches associated with this vein. The placement of the graft has the effect of excluding these branches, rather than having to address each one individually.

Note that vascular access related problems currently account for more than 25% of all hospitalizations among ESRD patients. Infections, peri-graft seroma, and pseudoaneurysm constitute less than 10-15% of graft failure. Instead, the majority is due to graft thrombosis, which is the result of disproportionate intimal hyperplasia at the venous outflow tract. The intimal hyperplasia responses occur (predominantly) in the proximal 2-3 cm of the vein just distal to the graft-vein anastomosis. The pathophysiological mechanisms behind the reactive intimal hyperplasia are believed to be due to increases of flow and to vascular injury. Anchor 12 achieves significant advantages over existing graft systems in that anchor 12 is secured within the vein and yields minimal radial forces. Radial forces must be accounted for because they can serve to injure vessels or the vein itself.

On the artery side of the graft (where the surgeon is facilitating a connection between a vein and an artery), body 14 is attached via anastomosis by suturing. A number of drugs may be disposed on, or within, body 14. For example, anti-coagulants, anti-thrombic, or growth factors may be used in such a scenario. The growth factors may be used in order to recruit endothelial progenitor cells that expedite recovery for a patient. The growth factors may also be used in order to encourage the formation of new structures (e.g. vessels) at this site.

Hence, the inside (or exterior) of the graft can be coated with, for example, a CD34 antigen. Additionally, any number of drugs can be used for coatings and wraps (e.g. sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, thalidomide, etc.).

Figure 4:
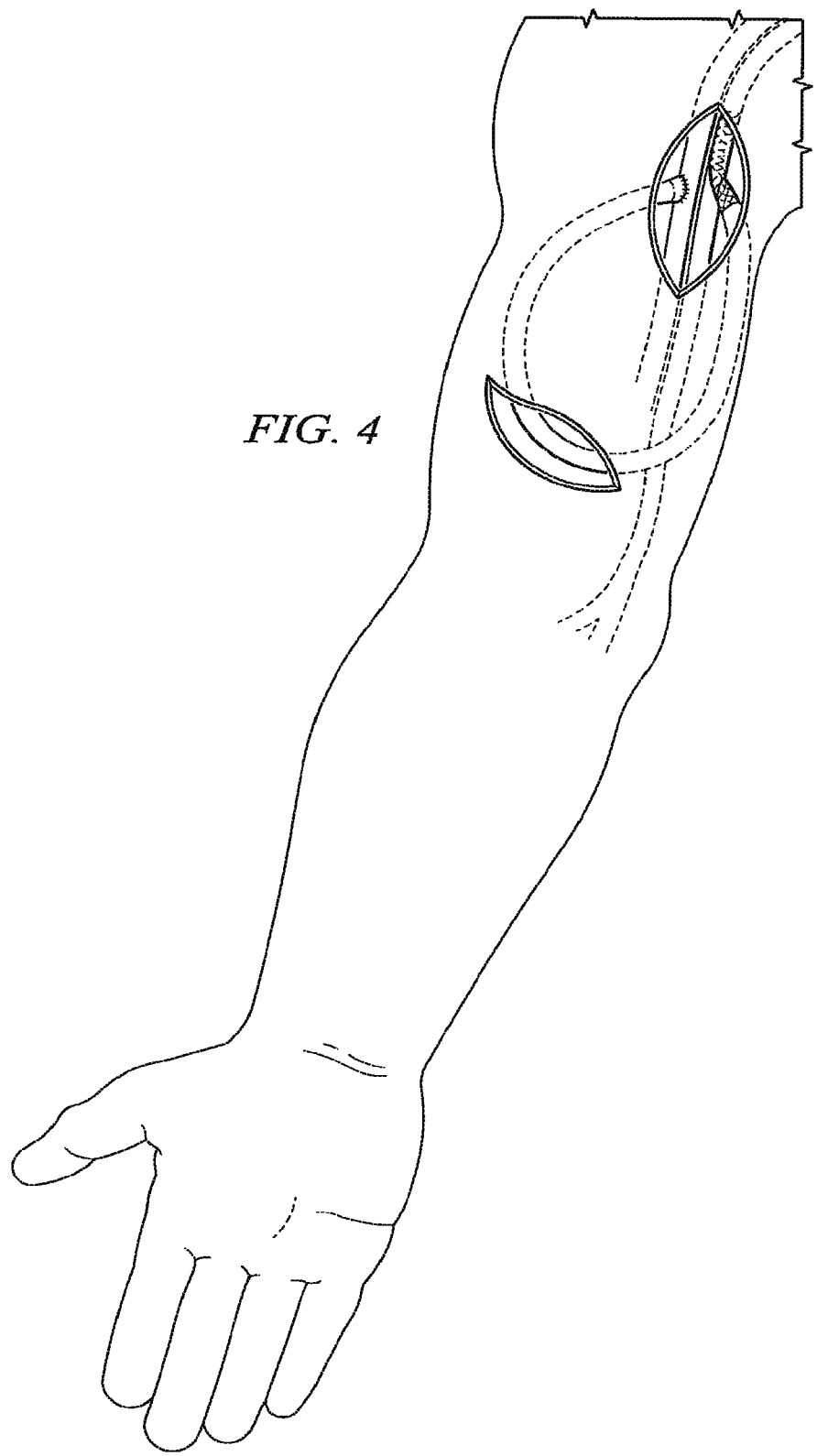
FIG. 4 is a simplified schematic diagram illustrating several connections that were created in a patient's arm using the graft of the present invention.

In operation of an example embodiment, consider the case of a patient who is experiencing kidney failure. The surgeon in this situation has elected to offer this patient a graft, as outlined herein. There are two incisions that are made by the surgeon: one at the artery and one at the vein. These incisions effectively localize the vein and the artery. A wire can then be inserted into the vein. The present invention can be positioned over the wire, whereby the graft is deployed. (Note that the present invention may also be deployed in a percutaneous fashion, which is further detailed below.) Anchor 12 is then suitably positioned within the vein. An effective positioning of anchor 12 operates to prevent back-slipping or bleeding on the venous side. The wire is subsequently removed from the surgical site. Body 14 can then be sutured to the artery. FIG. 4 is a simplified schematic diagram illustrating a completed procedure. In this instance, several connections were created by the surgeon in a patient's arm using the graft of the present invention.

In the percutaneous solution, entry can be from the venous or the arterial side. For purposes of discussion, the venous side solution is explained here. First, the target vein is accessed via a sheath in a conventional manner. Subsequently, a needle (which is specially designed to include a curve) that includes a hole is inserted into the sheath. Note that, for purposes of fluoroscopy, dye may also be injected into the patient, whereby a simple turnikit is used to stop the flow of blood.

With the target under fluoroscopy, the objective is to puncture the wall of the artery where the dye has accumulated. Then a wire can be inserted into the artery and the sheath can be advanced over the wire and directed to the artery. Thus, the sheath is now positioned between the vein and the artery. Now the environment is ready for the graft. As is described above, anchor 12 is positioned on the venous side. In addition, body 14 is coupled to the arterial side in any suitable manner (e.g. using a resistive force mechanism, using footers or legs that hold body 14 in place, using a funnel shaped design, etc.).

Turning now to the next set of FIGURES, FIGS. 5-12D are simplified schematic diagrams illustrating yet another set of dimensions and/or design possibilities of the graft of the present invention. For these example FIGURES, and to offer some example dimensions for a potential graft design, the approximate diameter of the graft is between 6-8 millimeters; the overall length of the of the graft is between 20-40 centimeters; the distal graft diameter delivered is <3 millimeters; the distal anchor graft diameter expanded is between 4-6 millimeters; the approximate length of the graft anchor into the vein is 2 centimeters; and the potential maximum length of the graft anchor outside the vein is 1.5 millimeters.

In addition, the graft material for this example design is ePTFE throughout the graft's length, where a NITINOL scaffold (about 3.5 centimeters) is provided to cover the distal end. A drug-eluting coating is provided to inhibit intimal hyperplasia. For example, the use of drugs such as rapamycin (or other similar drugs) may be used for their antiproliferative properties. Additionally, in the implementation of FIG. 5, a drug coating may be placed on both the exterior and the interior of the body of the graft. A section of ePTFE 60 is provided in combination with a NITINOL stent 62 with a coating.

FIGS. 6A and 6B illustrate a portion of the delivery system components for the graft of the present invention. A simple support-type catheter could be readily used in such applications. A plunger 70, along with a base 74, and a sheath could also be used in such an architecture. The delivery system of FIGS. 6A and 6B is unloaded at this point in time. A magnified view of a perforated sheath 72 of FIG. 6A is provided by FIG. 8. As highlighted above, the delivery of the device can be over the wire. A surgeon should have flexibility in retrieving and delivering the device, particularly in percutaneous procedures. Hence, the present invention can use any number of peelable components (e.g. peel-away sheaths) that alleviate some of the burden on the surgeon.

Figure 11A:
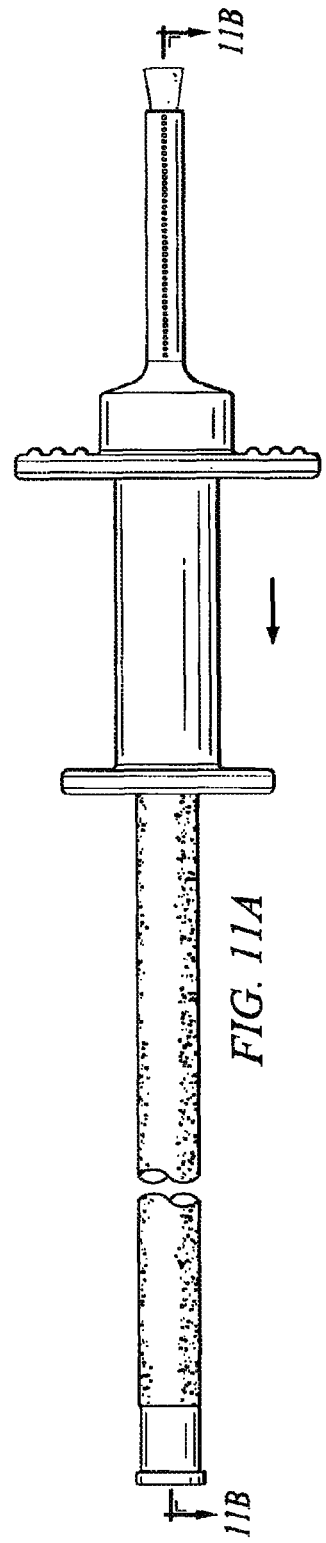
Figure 11B:
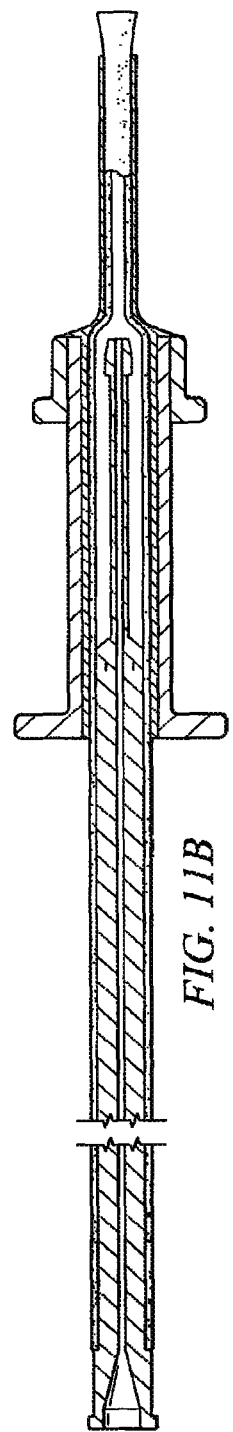

FIGS. 7A and 7B are simplified schematic diagrams that illustrate ancillary components of the delivery system of the present invention. An inner support 80 is provided along with a guidewire lumen 82 in conjunction with a luer fitting with a luer lock 84. FIGS. 10A and 10B show the delivery system fully loaded with the graft of the present invention, where FIG. 9 provides a magnified view of the tip of FIG. 10B. In these FIGURES, the anchor portion of the graft is in a compressed state. FIGS. 11A and 11B illustrate yet another example configuration before the device is deployed. Again, it should be reiterated that these design choices are not exhaustive and only offer the audience yet another potential construction of the graft.

FIGS. 12A-D illustrate yet another embodiment of the present invention. In this configuration, the proposed device is a balloon-expandable or self-expanding stent with a biodegradable cover or a coating of some type. Hence, instead of appearing as a simple stent design, the device includes an outer layer that gives it a cylindrical shape, as shown in the FIGURES.

In one sense, this particular embodiment is different from the aforementioned devices (discussed above) in that it is a full anchor design: capitalizing on the anchor technology discussed heretofore. In this complete anchor design, a suitable material (such as those coatings, polymers, and layers highlighted above, including the materials identified in the US patent numbers referenced previously) is disposed on the surface of the stent. In other instances, the material is placed within the stent, or any suitable combination being provided exterior to or within the device.

This device can be in the range of 8-200 millimeters, although such a parameter could be changed based on particular needs. This stent could be used in a multitude of environments, including: bypass grafts, dialysis grafts, carotid applications, vein grafts, peripheral arteries, as an esophageal and bronchial scaffold to deliver structure and drugs to a targeted area, or in any other vasculature or endovascular setting.

Figure 12A:
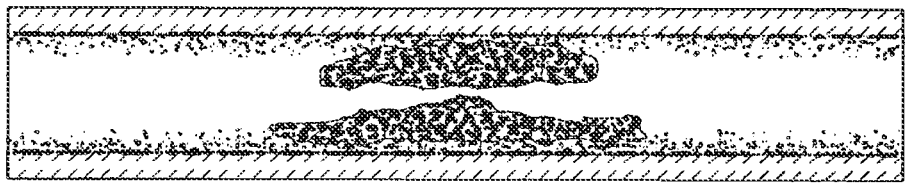
Figure 12B:
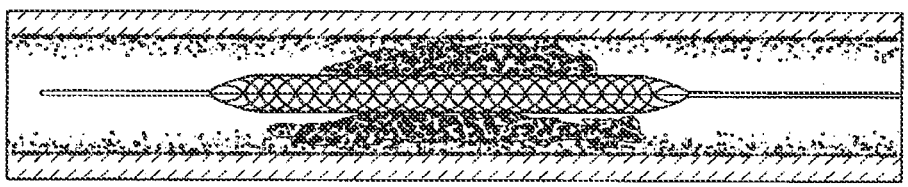
Figure 12C:
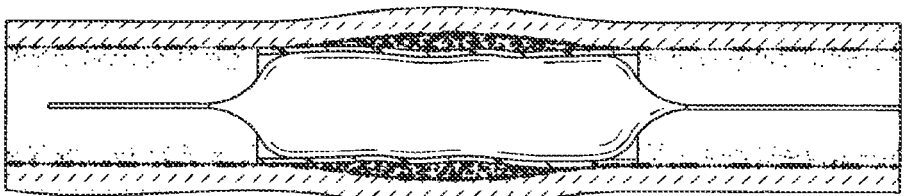
Figure 12D:
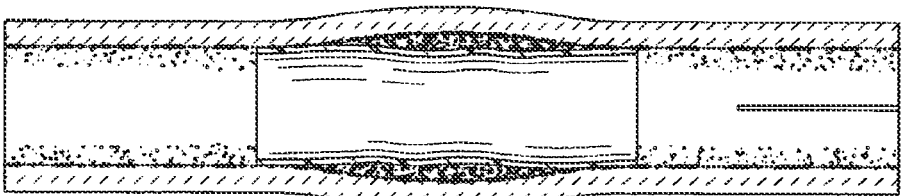

As highlighted in the corresponding FIGURES, the device in this situation could easily be placed percutaneously. FIG. 12A depicts a coronary artery blockage that is present; the darkened portions highlight the extent of the occlusion. In such a case, a wire is advanced over the blockage and then a stent balloon is subsequently advanced, as shown in FIG. 12B. FIG. 12C shows the balloon (or the self-expanding) element at the targeted area. FIG. 12D illustrates the device (i.e. the stent with the cover) being suitably positioned such that the pathway is now open and the occlusion has been resolved.

It is important to note that the stages and steps in the preceding FIGURES illustrate only some of the possible scenarios that may be executed by, or within, the architecture of the present invention. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered considerably. The preceding example flows have been offered for purposes of teaching and discussion. Substantial flexibility is provided by the proffered architecture in that any suitable arrangements, chronologies, configurations, and timing mechanisms may be provided without departing from the broad scope of the present invention.

Although the present invention has been described in detail with reference to particular embodiments in FIGS. 1-12D, it should be understood that various other changes, substitutions, and alterations may be made hereto without departing from the sphere and scope of the present invention. For example, although the preceding FIGURES have referenced a number of components as participating in the numerous outlined procedures, any suitable equipment or relevant tools may be readily substituted for such elements and, similarly, benefit from the teachings of the present invention. These may be identified on a case-by-case basis, whereby a certain patient may present a health risk factor while another (with the same condition) may not. Hence, the present device may be designed based on particular needs with specific scenarios envisioned.

Additionally, although the preceding FIGURES have described a body-anchor combination, another possibility of the present invention could be two anchors. In such a case, both anchors would seat directly in the vessel. It should also be noted yet again that the present invention is not limited to vein-artery connections, as vein-vein and artery-artery scenarios can certainly be accommodated by the present invention.

It is also imperative to note that although the present invention is illustrated as implicating a number of conventional procedures, the present invention could be completely percutaneous, as highlighted above. In essence, the present invention may be applicable to a multitude of environments in which a viable conduit is needed.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. An apparatus, comprising:
 a graft for coupling two vascular conduits, wherein the graft includes:
   a curved anchor system having an expandable end adapted to be coaxially received within one of the conduits such that the expandable end applies a resistive force to the one conduit when the expandable end is radially expanded to have a greater inner dimension; and
   a body element coupled to the curved anchor system, wherein the anchor system forms an arc at an opening of the one conduit such that the body element is angled outwardly from the opening, and wherein the curved anchor system is substantially self-sealing at the one conduit, wherein an abrasive material of the anchor system provides a frictional resistive force to inhibit movement of the anchor system relative to the one conduit when the anchor system is radially expanded within the one conduit, wherein the anchor system comprises a biodegradable stent, wherein a delivery system is used to deliver the graft to a target location, wherein the delivery system includes a plunger and a base that is coupled to the plunger, wherein actuation of the plunger can cause the graft to be released.

2. The apparatus of claim 1, wherein the body element and the curved anchor system are integrally formed.

3. The apparatus of claim 1, wherein the body element is at least partially biodegradable.

4. The apparatus of claim 1, wherein the stent includes a drug, which covers either an external or an internal surface of the stent.

5. The apparatus of claim 1, wherein the covers the curved anchor system and the body element.

6. The apparatus of claim 1, wherein the expandable end of the curved anchor system is either self-expandable or balloon-expandable.

7. The apparatus of claim 1, wherein the graft includes internal scaffolding to provide reinforcement to the graft.

8. The apparatus of claim 1, wherein the body element or the curved anchor system includes a coating, a fibrous material, or a wrap that can be used for drug loading.

9. The apparatus of claim 8, wherein the curved anchor system is drug eluting.

10. An apparatus, comprising:
 a graft for coupling two vascular conduits, wherein the graft includes:
   a curved anchor system forming an arc at an opening of the conduits, the curved anchor system including an expandable end; and
   a body element integrally formed with the curved anchor system into a continuous piece,
   wherein when the expandable end is positioned through an opening of one conduit with at least a portion of the anchor system coaxially aligned with the one conduit and with the expandable end radially expanded therein, the expandable end applies a resistive force to the one conduit and the body element is in fluid communication with the one conduit without needing sutures at the opening, wherein the anchor system comprises a biodegradable stent, wherein a delivery system is used to deliver the graft to a target location, wherein the delivery system includes a plunger and a base that is coupled to the plunger, wherein actuation of the plunger can cause the graft to be released.

11. The apparatus of claim 10, wherein the body element is angled outwardly from the opening of the one conduit.

12. The apparatus of claim 11, wherein the curved anchor system is substantially self-sealing at the one conduit.

13. The apparatus of claim 10, wherein the graft further includes an outer cover surrounding the curved anchor system.

14. The apparatus of claim 13, wherein the outer cover is adapted to deliver drug therapy to the one conduit.

15. The apparatus of claim 13, further comprising:
an inner cover opposing the outer cover and defining a space therebetween sized to receive the stent.

16. The apparatus of claim 15, wherein the inner cover is adapted to deliver drug therapy to the one conduit.

17. The apparatus of claim 10, further comprising:
an expandable stent extending along the body element.

18. The apparatus of claim 10, wherein the curved anchor system is substantially self-sealing at the one conduit.

19. An apparatus, comprising:
a graft for coupling two vascular conduits within a patient, wherein the graft includes:
an anchor system that forms an arc at an opening of one end of the conduits;
a body element coupled to the anchor system, wherein the anchor system comprises a biodegradable stent;
a delivery system used to deliver the graft to a target location, wherein the delivery system includes a plunger and a base that is coupled to the plunger, wherein actuation of the plunger can cause the graft to be released.

20. The apparatus of claim 19, wherein the delivery system further includes a perforated splittable sheath.

21. The apparatus of claim 1, wherein the abrasive material is one of a coating on the anchor system or a structure of the anchor system.

* * * * *